(12) United States Patent
Yelle et al.

(10) Patent No.: US 6,498,171 B2
(45) Date of Patent: Dec. 24, 2002

(54) HYDROXYOMEPRAZOLE COMPOSITIONS

(75) Inventors: William E. Yelle, Littleton, MA (US); Dean A. Handley, Westborough, MA (US)

(73) Assignee: Sepracor Inc., Marlborough, MA (US)

(*) Notice: Subject to any disclaimer, the term of this patent is extended or adjusted under 35 U.S.C. 154(b) by 0 days.

(21) Appl. No.: 09/927,954

(22) Filed: Aug. 10, 2001

(65) Prior Publication Data

US 2002/0010196 A1 Jan. 24, 2002

Related U.S. Application Data

(62) Division of application No. 09/699,597, filed on Oct. 30, 2000, now Pat. No. 6,294,586, which is a continuation of application No. PCT/US99/09814, filed on May 5, 1999.
(60) Provisional application No. 60/084,258, filed on May 5, 1998.

(51) Int. Cl.[7] ............................................. A61K 31/44
(52) U.S. Cl. ..................... 514/338; 514/926; 514/927
(58) Field of Search ................................ 514/338, 926, 514/927

(56) References Cited

PUBLICATIONS

Http://www.pdrel.com/pdr/static.htm?path=pdrel/pdr/04002575.htm pp. 1–38.*

Prof. Sally Boudinot, Chemcases.com, Kennesaw State University, 17. Penicillin, http://chemcases.com/pheno/pheno17.htm, pp. 1–8.*

* cited by examiner

*Primary Examiner*—Shep K. Rose
*Assistant Examiner*—Donna Jagoe
(74) *Attorney, Agent, or Firm*—Heslin Rothenberg Farley & Mesiti P.C.

(57) ABSTRACT

Methods and compositions are disclosed utilizing hydroxyomeprazole for the treatment of ulcers in humans. Hydroxyomeprazole exhibits a lessened liability toward drug-drug interactions than omeprazole and a more predictable dosing regimen than omeprazole. Hydroxyomeprazole is also useful for the treatment of gastroesophageal reflux and other conditions related to gastric hypersecretion such as Zollinger-Ellison Syndrome.

6 Claims, No Drawings

HYDROXYOMEPRAZOLE COMPOSITIONS

CROSS REFERENCE TO RELATED APPLICATIONS

This application is a divisional of U.S. Ser. No. 09/699,597, filed Oct. 30, 2000, now U.S. Pat. No. 6,294,586, which was a continuation of PCT application PCT/US99/09814, filed May 5, 1999, and published in English as WO 99/56746 on Nov. 11, 1999. PCT/US99/09814 claimed the priority of U.S. provisional application No. 60/084,258, filed May 5, 1998. The entire disclosures of all are incorporated herein by reference.

FIELD OF THE INVENTION

This invention relates to compositions of matter containing hydroxyomeprazole. The invention also relates to methods of treating and preventing ulcers, treating other conditions related to gastric hypersecretion, and treating psoriasis.

BACKGROUND OF THE INVENTION

Omeprazole I is an orally active, potent,

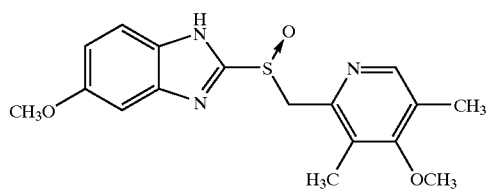

irreversible inhibitor of $H^+,K^+$-ATPase. It is commercially available in the form of Prilosec® delayed release capsules from Astra Merck Inc. The compound is one of the class of compounds known as gastric "proton pump" inhibitors. These compounds are weak organic bases which diffuse passively from the plasma into the acid-containing intracellular canaliculi of gastric parietal cells. At the low pH found in the lumen of these canaliculi, the protonated compounds rearrange to form pyridinium sulfenamides, which react with sulfhydryl groups present on the ATPase localized in the membranes lining the intracellular canaliculi. The alkylation of the sulfhydryl inhibits the ability of the enzyme to catalyze the secretion of $H^+$ into the lumen in exchange for $K^+$ ions. This inhibition results in an overall reduction in hydrochloric acid secretion by the parietal cells into the cavity of the stomach, thus increasing intragastric pH. As a consequence of reduced acidity in the stomach, the activity of the proteolytic enzyme pepsin is also markedly decreased. Because the proton pump is the final step in acid production and the compounds of this class combine covalently with the associated $H^+,K^+$-ATPase, a profound and prolonged inhibition of gastric acid secretion can be achieved.

Proton pump inhibitors have also been reported as useful in treating psoriasis. [See PCT application WO95/18612]

The $C_{max}$ of racemic omeprazole is at about 0.5 to 3.5 hours in humans, and the serum half-life is about 30 to 60 minutes, although this is highly variable, as discussed below. The major metabolites in human serum are 5-hydroxyomeprazole II (referred to as hydroxyomeprazole herein) and omeprazole sulfone III.

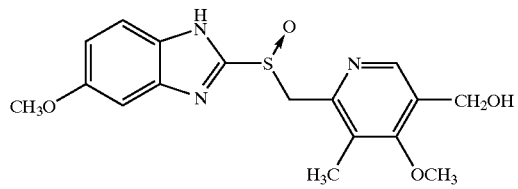

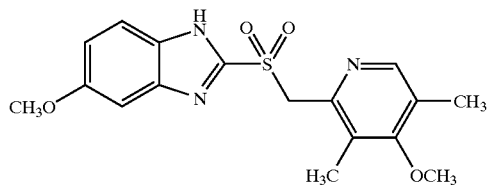

The two major primary metabolites, omeprazole sulfone and 5-hydroxyomeprazole, are formed by cytochromes P450 3A (CYP3A) and 2C19 (CYP2C19), respectively. Both metabolites undergo further metabolism to the common metabolite 5-hydroxyomeprazole sulfone via CYP2C19 and CYP3A, respectively. Thus, both CYP enzymes are sequentially—but alternatively—involved in omeprazole metabolism. CYP2C19, the S-mephenytoin hydroxylase, is polymorphically expressed in the human population. The mutant allele constitutes the recessive trait. Homozygous carriers of the mutation completely lack CYP2C19 and are referred to as poor metabolizers (PM's); persons homozygous and heterozygous for the "normal" allele are extensive metabolizers (EM's). A hereditary deficiency of the alternative enzyme, CYP3A, has not been demonstrated in the human population.

The individual enantiomers of racemic omeprazole are differentially metabolized by CYP 2C19. (+) Omeprazole is rapidly hydroxylated; (−) is not. The individual enantiomers of racemic omeprazole do not appear to be differentially metabolized by CYP 3A4; both are oxidized to the achiral sulfone at comparable rates. This results in a divergence in serum metabolite concentration profiles between poor metabolizers and extensive metabolizers. The mean 8-hour AUC ratio of (+)-omeprazole/(+)-hydroxyomeprazole is 30 times higher and the 8-hour AUC of omeprazole sulfone is more than 10 times higher in poor metabolizers than are the corresponding parameters in extensive metabolizers.

It would be desirable to find a compound with the advantages of omeprazole which would provide a more predictable dosage regimen in the patient population and that would decrease the chances for drug-drug interactions.

SUMMARY OF THE INVENTION

This invention relates to the use of hydroxyomeprazole for treating ulcers of the stomach, duodenum and esophagus, gastroesophageal reflux diseases, Zollinger-Ellison Syndrome, and other disorders including those that would benefit from an inhibitory action on gastric acid secretion. Hydroxyomeprazole inhibits the $H^+,K^+$-ATPase associated with the gastric proton pump and the resulting secretion of gastric acid by parietal cells providing therapy in diseases associated with gastric hyperacidity. The invention also relates to a method of treating psoriasis using hydroxyomeprazole. Hydroxyomeprazole provides a more predictable dosage regimen in the patient population and decreases the chances for drug-drug interactions by avoiding oxidative metabolism for which the cytochrome P450 2C19 enzyme system is required.

The invention also relates to certain pharmaceutical compositions containing hydroxyomeprazole.

DETAILED DESCRIPTION OF THE INVENTION

The active compound of these compositions and methods is hydroxyomeprazole. The preparation of racemic hydroxyomeprazole has been described by Renberg et al. [*Drug Metabolism and Disposition,* 17:1, 69–76 (1989)], the disclosure of which is incorporated herein by reference. Chemically, the compound of the invention is 2-[[(5-hydroxymethyl-4-methoxy-3-methyl-2-pyridinyl)methyl]sulfinyl-[1H]-benzimidazole (II), hereinafter referred to as hydroxyomeprazole. Hydroxyomeprazole is not presently commercially available.

Hydroxyomeprazole possesses a center of asymmetry at the sulfoxide sulfur, giving rise to two enantiomers. Throughout the instant disclosure, when the term is not otherwise modified, hydroxyomeprazole includes the (+) enantiomer, the (−) enantiomer and any mixture of the two. The preparation of the individual enantiomers of the parent, omeprazole, has been described in the literature, but the enantiomers of hydroxyomeprazole have been previously disclosed only as identities assigned to peaks on a chromatogram. The individual enantiomers of hydroxyomeprazole can be obtained by asymmetric oxidation of the thioether precursor and bioreduction of the racemate to eliminate one or the other enantiomer in analogous fashion to the procedure described for lansoprazole in PCT applications WO 9602535 and 9617077; the disclosures of both are incorporated herein by reference. The thioether precursor is available by the method of Renberg (op. cit.).

The literature does not appear to provide any reports of testing in vivo or of the administration of racemic hydroxyomeprazole or either of its enantiomers to human subjects. The inhibitory effects of omeprazole and rac-hydroxyomeprazole on aminopyrine uptake in isolated gastric glands have been reported; the $IC_{50}$ of racemic omeprazole was 0.48 $\mu$M and the $IC_{50}$ of racemic hydroxyomeprazole was 33 $\mu$M. Renberg et al. [*Drug Metabolism and Disposition,* 17:1, 69–76 (1989)] concluded that the contribution of race-hydroxy-omeprazole to the pharmacological response to treatment with omeprazole in humans was probably insignificant.

It has now been discovered that hydroxyomeprazole is a superior agent for treating ulcers of the stomach, duodenum and esophagus, gastroesophageal reflux diseases, Zollinger-Ellison Syndrome, psoriasis and other disorders, including those that would benefit from an inhibitory action on $H^+,K^+$-ATPase in that it provides this effective treatment while exhibiting fewer or less severe adverse effects than omeprazole, less potential for drug-drug interactions than omeprazole and a more predictable dosing regimen than omeprazole. Adverse effects of omeprazole include hepatocellular neoplasia, gastric carcinoids, headache, diarrhea and skin alterations.

The present invention encompasses a method of treating ulcers, which comprises administering to a human in need of such therapy, an amount of hydroxyomeprazole, or a pharmaceutically acceptable salt thereof, said amount being sufficient to alleviate the symptoms of ulcers.

The present invention also encompasses an oral antiulcer composition for the treatment of a human in need of antiulcer therapy, which comprises a pharmaceutically acceptable carrier for oral administration and a therapeutically effective amount of hydroxyomeprazole, or a pharmaceutically acceptable salt thereof. Preferably the composition is in the form of a tablet or capsule, and the amount of hydroxyomeprazole in the tablet or capsule is preferably about 100–500 mg.

The present invention further encompasses a method of treating gastroesophageal reflux disease and of treating conditions caused by or contributed to by gastric hypersecretion. Conditions associated with hypersecretion in humans may include, but are not limited to, Zollinger-Ellison syndrome.

The present invention further encompasses a method of treating psoriasis.

Utilizing hydroxyomeprazole results in enhanced dosage predictability and an improved therapeutic index. In particular, hydroxyomeprazole exhibits less variation in the patient population between so-called extensive metabolizers and poor metabolizers than does omeprazole.

The term "treating ulcers" as used herein means treating, alleviating or palliating such conditions, and thus providing relief from the symptoms of nausea, heartburn, post-prandial pain, vomiting, and diarrhea.

The term "a method for treating gastroesophageal reflux diseases in a human" as used herein means treating, alleviating or palliating the conditions that result from the backward flow of the stomach contents into the esophagus.

The term "treating a condition caused, or contributed to, by gastric hypersecretion in a human" as used herein means treating, alleviating or palliating such disorders associated with hypersecretion, thus providing relief from the symptoms of the aforementioned conditions. Zollinger-Ellison Syndrome is among the conditions caused by or contributed to by hypersecretion.

The term "treating psoriasis" as used herein means treating, alleviating or palliating the condition, and thus providing relief from the symptoms of pruritis, epidermal scaling, itching and burning.

The term "optically pure" as used herein means that the compositions contain at least 90% by weight of one enantiomer and 10% by weight or less of the other. In a more preferred embodiment the term "substantially optically pure" means that the composition contains at least 99% by weight of one enantiomer, and 1% or less of the opposite enantiomer. In the most preferred embodiment, the term "substantially optically pure" as used herein means that the composition contains greater than 99% by weight of a single enantiomer. These percentages are based upon the total amount of hydroxyomeprazole in the composition.

The magnitude of a prophylactic or therapeutic dose of hydroxyomeprazole in the acute or chronic management of disease will vary with the severity of the condition to be treated and the route of administration. The dose and perhaps the dose frequency will also vary according to the age, body weight and response of the individual patient. In general, the total daily dose range for hydroxy-omeprazole for the conditions described herein is from about 50 mg to about 1500 mg in single or divided doses. Preferably a daily dose range should be about 500 mg to about 1000 mg in single or divided doses. In managing the patient, the therapy should be initiated at a lower dose, perhaps at about 50 mg and increased up to about 1000 mg or higher depending on the patient's global response. It is further recommended that children and patients over 65 years and those with impaired renal or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The terms "an amount sufficient to alleviate or palliate ulcers" "an amount sufficient to alleviate the symptoms of gastroesophageal reflux", "an amount sufficient to alleviate gastric hypersecretion" and "an amount sufficient to treat psoriasis" are encompassed by the above-described dosage amounts and dose frequency schedule.

The relative activity, potency and specificity of hydroxyomeprazole both as a gastric antisecretory agent and as a plasma gastrin elevating agent can be determined by a pharmacological study in animals according to the method of Decktor et al. [*J. Pharmacol. Exp. Ther.* 249, 1–5 (1989)]. The test provides an estimate of relative activity, potency and, through a measure of specificity, an estimate of therapeutic index. Fasted rats, implanted with a gastric cannula, receive single oral or parenteral doses of (+) hydroxyomeprazole, (−) hydroxyomeprazole or racemate, 1 hour before collection of gastric juice over a four hour period. Acid output and pH are then determined on each sample. Dose response evaluations are performed with each compound to determine the lowest dose which inhibits acid output by at least 95% and maintains gastric pH above 7.0. Plasma gastrin levels are then determined in a second group of rats treated with the doses selected in the first series of tests. Blood samples are taken for analyses over the five hour period after dosing, and both peak level as well as area-under-the-curve analyses of the gastrin responses are made. These responses are then analyzed statistically using Student's "t" test to assess whether equivalent antisecretory doses show differences in gastrin responses.

Any suitable route of administration may be employed for providing the patient with an effective dosage of hydroxyomeprazole. Rectal, parenteral (subcutaneous, intramuscular, intravenous), transdermal, and like forms of administration are possible, but oral administration is preferred. Oral dosage forms include tablets, troches, dispersions, suspensions, solutions, capsules, and the like.

The pharmaceutical compositions of the present invention comprise hydroxyomeprazole as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic bases. Since the compound of the present invention is a weak acid and is unstable at low pH, salts may be prepared from pharmaceutically acceptable non-toxic bases including inorganic and organic bases. Suitable pharmaceutically acceptable base addition salts for the compound of the present invention include metallic salts of aluminum, calcium, lithium, magnesium, potassium, sodium, titanium and zinc or organic salts made from lysine, N,N'-dibenzylethylenediamine, chloroprocaine, choiine, diethanolamine, ethylenediamine, meglumine (N-methylglucamine) and procaine. Sodium salts are preferred.

The compositions of the present invention include suspensions, solutions, elixirs and solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations. It has been found that the inclusion of mannitol and of basic salts of calcium and magnesium in the compositions allows the preparation of tablets and capsules that retain good stability. Because of the acid instability of hydroxyomeprazole, it is usually advantageous to coat oral solid dosage forms with an enteric or delayed-release coating. This may be accomplished by standard aqueous or nonaqueous techniques. Oral dosage forms suitable for hydroxyomeprazole are described in U.S. Pat. No. 5,035,899 and in PCT applications WO96/01624, WO97/12580 and WO97/25030, the disclosures of which are incorporated herein by reference.

In addition to the common dosage forms set out above, the compounds of the present invention may also be administered by controlled release formulations, which are well known in the art. Compositions suitable for rectal administration are described in European Application 645140, the disclosure of which is incorporated herein by reference.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent. Desirably, each tablet or capsule contains about 100 mg to 500 mg of the active ingredient.

An enteric coating, such as the polyacrylate Eudragit L® and Eudragit S® series, is applied by spray coating the tablets, preferably with an aqueous dispersion of the coating polymer. Tablets of other strengths may be prepared by altering the ratio of active ingredient to the excipients or to the final weight of the tablet. Oral, as well as parenteral, sustained release drug delivery systems are well known to those skilled in the art, and general methods of achieving sustained release of orally or parenterally administered drugs are found in any standard pharmacy school textbook, for example *Remington: The Science and Practice of Pharmacy*. Chapter 94 of the 19th edition of Remington entitled "Sustained-Release Drug Delivery Systems" describes the more common types of oral and parenteral sustained-release dosage forms (pages 1660–1675.) The disclosure is incorporated herein by reference.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampules and vials, and may be stored in a freeze-dried (lyophilized) condition requiring only the addition of a sterile liquid carrier. for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

The invention is further defined by reference to the following examples describing in detail the preparation of the compositions of the present invention. It will be apparent to those skilled in the art that many modifications, both to materials and methods, may be practiced without departing from the invention.

EXAMPLES

Example 1

250 mg Tablets

| Composition per tablet: | |
|---|---|
| hydroxyomeprazole | 250 mg |
| croscarmellose | 60 mg |
| colloidal silicon dioxide | 8 mg |
| magnesium stearate | 1 mg |
| microcrystalline cellulose | 190 mg |
| croscarmellose | 15 mg |
| talc | 10 mg |
| Total | 534 mg |

Example 1

Hydroxyomeprazole and silicon dioxide are dry mixed, the first portion of croscarmellose is added and the mixture is further dry mixed. The magnesium stearate is added, dry mixed and the mixture is run through a roller compactor and mill. The resulting dry granulate is mixed with the remaining three ingredients and compressed into tablets.

Example 2

200 mg Tablets

| Composition per unit dosage: | |
|---|---|
| hydroxyomeprazole | 200 mg |
| pregelatinized starch | 200 mg |
| microcrystalline cellulose | 25 mg |

| -continued | |
|---|---|
| Composition per unit dosage: | |
| povidone | 15 mg |
| coscarmellose | 10 mg |
| magnesium stearate | 3.75 mg |
| FD&C yellow #2 lake | 2.5 mg |
| Water | (5 mL) |
| Total | 456.25 mg |

Example 2

The ingredients above are mixed well in the proportions shown in a high shear mixer until uniform granules result. The mixture is tray-dried at 40° C. under vacuum until the desired consistency is reached. The granules are milled to less than 60 mesh using a screen mill and compressed into tablets.

Example 3

Enteric Coating

| Enteric coating composition: | |
|---|---|
| Eudragit L-30D | 138 mg (solids 41.4 mg) |
| Talc | 4.1 mg |
| Polyethylene glycol 5000 | 12.4 mg |
| Tween 80 | 2.1 mg |
| Water | 250 µl |

Enteric tablets are produced by coating the tablets obtained in Example 2 with the enteric coating composition shown in a pan coater.

Example 4

Aqueous Suspension for Injection

A suspending vehicle is prepared from the following materials:

| Polyethylene glycol 4000 | 30 gm. |
|---|---|
| Potassium chloride | 11.2 gm. |
| Polysorbate 80 | 2 gm. |
| Methylparaben | 0.2 gm. |
| Water for injection q.s. | 1000 mL. |

The parabens are added to a major portion of the water and are dissolved therein by stirring and heating to 65° C. The resulting solution is cooled to room temperature and the remainder of the ingredients are added and dissolved. The balance of the water to make up the required volume is then added and the solution sterilized by filtration. The sterile vehicle thus prepared is then mixed with 3 gm of hydroxyomeprazole sodium salt, which has been previously reduced to a particle size less than about 10 microns and sterilized with ethylene oxide gas. The mixture is passed through a sterilized colloid mill and filled under aseptic conditions into sterile containers which are then sealed.

What is claimed is:

1. A pharmaceutical composition in the form of a tablet or capsule comprising a pharmaceutically acceptable carrier for oral therapy and a therapeutically effective amount of hydroxyomeprazole or a pharmaceutically acceptable salt thereof.

2. A pharmaceutical composition according to claim 1 comprising a pharmaceutically acceptable carrier for oral therapy and a therapeutically effective amount of optically pure (+)-hydroxyomeprazole or a pharmaceutically acceptable salt thereof.

3. A pharmaceutical composition according to claim 1 comprising a pharmaceutically acceptable carrier for oral therapy and a therapeutically effective amount of optically pure (−)-hydroxyomeprazole or a pharmaceutically acceptable salt thereof.

4. A pharmaceutical composition according to claim 1 comprising a pharmaceutically acceptable carrier for oral therapy and a therapeutically effective amount of racemic hydroxyomeprazole or a pharmaceutically acceptable salt thereof.

5. A pharmaceutical composition comprising a pharmaceutically acceptable carrier for parenteral therapy and a therapeutically effective amount of optically pure (+)-hydroxyomeprazole or a pharmaceutically acceptable salt thereof.

6. A pharmaceutical composition comprising a pharmaceutically acceptable carrier for parenteral therapy and a therapeutically effective amount of optically pure (−)-hydroxyomeprazole or a pharmaceutically acceptable salt thereof.

* * * * *